(12) United States Patent
Kabir et al.

(10) Patent No.: US 9,772,338 B2
(45) Date of Patent: Sep. 26, 2017

(54) MATERIALS AND METHODS FOR THE DETECTION OF TRACE AMOUNTS OF SUBSTANCES IN BIOLOGICAL AND ENVIRONMENTAL SAMPLES

(71) Applicants: Abuzar Kabir, Miami, FL (US); Kenneth G. Furton, Homestead, FL (US)

(72) Inventors: Abuzar Kabir, Miami, FL (US); Kenneth G. Furton, Homestead, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/298,776

(22) Filed: Oct. 20, 2016

(65) Prior Publication Data

US 2017/0108520 A1    Apr. 20, 2017

Related U.S. Application Data

(60) Provisional application No. 62/243,977, filed on Oct. 20, 2015.

(51) Int. Cl.
*G01N 33/94* (2006.01)
*G01N 33/04* (2006.01)
*B01J 20/26* (2006.01)
*C08G 77/06* (2006.01)

(52) U.S. Cl.
CPC ........ *G01N 33/9446* (2013.01); *B01J 20/268* (2013.01); *C08G 77/06* (2013.01); *G01N 33/04* (2013.01); *G01N 2600/00* (2013.01)

(58) Field of Classification Search
CPC ............... G01N 33/9446; G01N 33/04; G01N 2600/00; C08G 77/06; B01J 20/268
See application file for complete search history.

(56) References Cited

U.S. PATENT DOCUMENTS

2012/0070879 A1 *   3/2012   Sallitt ................ G01N 33/9446
                                                    435/252.1

FOREIGN PATENT DOCUMENTS

FR      WO 2014102209 A1 *   7/2014   ............. A61Q 5/006
WO      WO 2014062632 A1 *   4/2014   ........... C12H 1/0424

OTHER PUBLICATIONS

Liu et al. "Synthesis and characterization of molecularly imprinted polymers for recognition of ciprofloxacin." Front. Chem. China (2008) 3 378-383.*

Shimelis et al. "Detection of Low Level of Chloramphenicol in Milk and Honey with MIP SPE and LC-MS-MS." Supelco Presentation (2007).*
Li, Junjie et al. "Molecularly imprinted polymers on the surface of silica microspheres via sol-gel method for the selective extraction of streptomycin in aqueous samples." J. Sep. Sci. (2013) 36 1142-1148.*
Alizadeh, Taher et al., "Selective determination of chloramphenicol at trace level in milk samples by the electrode modified with molecularly imprinted polymer." *Food Chemistry*, Feb. 15, 2012, 130(4): Abstract.
Boyd, B. et al., "Development of an improved method for trace analysis of chloramphenicol using molecularly imprinted polymers." *J Chromatogr. A.*, Dec. 7, 2007, 1174(1-2): Abstract.
Buszewski, Boguslaw et al., "Past, Present, and Future of Solid Phase Extraction: A Review." *Critical Reviews in Analytical Chemistry*, Jun. 13, 2012, 42(3): Abstract.
Chen, Ligang et al., "Magnetic molecularly imprinted polymer extraction of chloramphenicol from honey." *Analytical Methods*, Nov. 2013, 141(1): 23-28.
Chen, Lingxin et al., "Recent advances in molecular imprinting technology: current status, challenges and highlighted applications." *Chem. Soc. Rev.*, 2011, 40: 2922-2942.
Cheng, Won Jo et al., "Molecular imprinted polymers for separation science: A review of reviews." *J. Sep. Sci.*, Feb. 2013, 36: 609-628.
Commission, "Commission Decision of Mar. 13, 2003 amending Decision 2002/657/EC as regards the setting of minimum required performance limits (MRPLs) for certain residues in food of animal origin." *Official Journal of the European Union*, 2003, 17-18.
Falagas, Matthew E. et al., "Potential of old-generation antibiotics to address current need for new antibiotics." *Expert Rev. Anti Infect. Ther.*, 2008, 6(5): 593-600.
Farre, Marinella et al., "Green analytical chemistry in the determination of organic pollutants in the aquatic environment." *Trends in Analytical Chemistry*, 2010, 29(11): 1347-1362.
Hu, Jia-Hong et al., "Surface molecularly imprinted polymers with synthetic dummy template for simultaneously selective recognition of nine phthalate esters." *Journal of Chromatography A*, Feb. 21, 2014, 1330: 6-13.
Karageorgou, E. et al., "Development and validation according to European Union Decision 2002/657/EC of an HPLC-DAD method for milk multi-residue analysis of penicillins and amphenicols based on dispersive extraction by QuEChERS in MSPD format." *J Sep Sci.*, Aug. 2011, 34(15): Abstract.

(Continued)

*Primary Examiner* — Christopher A Hixson
(74) *Attorney, Agent, or Firm* — Saliwanchik, Lloyd & Eisenschenk

(57) ABSTRACT

The subject invention provides chemical compositions and synthesis strategies to create molecularly imprinted polymers (MIPs) via sol-gel processes. In a specific embodiment, the subject invention utilizes a(n) organic, inorganic, or metallic template analyte to create a hybrid organic-inorganic or inorganic three-dimensional network possessing cavities complementary to the shape, size, and functional orientation of the template molecule or ions. The subject invention further pertains to the use of the novel MIPs as selective solid phase extraction (SPE) sorbents for pre-concentration and clean-up of trace substances in biological and environmental samples. Synthesis of other molecularly imprinted polymers with environmental, pharmaceutical, chemical, clinical, toxicological, and national security implications can be conducted in accordance with the teachings of the subject invention.

16 Claims, 13 Drawing Sheets

(56) References Cited

OTHER PUBLICATIONS

Karageorgou, E. et al., "Multiresidue LC-MS/MS analysis of cephalosporins and quinolones in milk following ultrasound-assisted matrix solid-phase dispersive extraction combined with the quick, easy, cheap, effective, rugged, and safe methodology." *J. Sep. Sci.*, Jun. 2013, 36(12): Abstract.

Karageorgou, E. et al., "Ultrasound-assisted dispersive extraction for the high pressure liquid chromatographic determination of tetracyclines residues in milk with diode array detection." *Analytical Methods*, May 2014, 150: 328-334.

Karageorgou, E. et al., "Ultrasound-assisted matrix solid phase dispersive extraction for the simultaneous analysis of β-lactams (four penicillins and eight cephalosporins) in milk by high performance liquid chromatography with photodiode array detection." *J. Sep. Sci.*, Oct. 2012, 35(19): Abstract.

Li, Junjie et al., "Molecularly imprinted polymers on the surface of silica microspheres via sol-gel method for the selective extraction of streptomycin in aqueous samples." *J. Sep. Sci.*, Mar. 2013, 36(6): Abstract.

Liu, Guoyan et al., "Towards the development of a sensitive electrochemical sensor for the determination of chloramphenicol residues in milk." *Analytical Methods*, 2015, 7(4): Abstract.

Mohamed, R. et al., "Advantages of molecularly imprinted polymers LC-ESI-MS/MS for the selective extraction and quantification of chloramphenicol in milk-based matrixes. Comparison with a classical sample preparation." *Anal. Chem.*, Dec. 15, 2007, 79(24): Abstract.

Nicolich, Rebecca S. et al., "Food safety evaluation: Detection and confirmation of chloramphenicol in milk by high performance liquid chromatography-tandem mass spectrometry." *Analytica Chimica Acta*, Apr. 13, 2006, 565(1): Abstract.

Ramos, Macarena et al., "Chloramphenicol Residues in Food Samples: Their Analysis and Stability During Storage." *J Chromatogr A.*, 2003, 26(15): Abstract.

Rejtharova, M. et al., "Determination of chloramphenicol in urine, feed water, milk and honey samples using molecular imprinted polymer clean-up." *J Chromatogr A.*, Nov. 13, 2009, 1216(46): Abstract.

Rezende, DR et al., "Simultaneous determination of chloramphenicol and florfenicol in liquid milk, milk powder and bovine muscle by LC-MS/MS." *Food Addit Contam Part A Chem Anal Control Expo Risk Assess.*, 2012, 29(4): Abstract.

Samanidou, Victoria et al., "Fast extraction of amphenicols residues from raw milk using novel fabric phase sorptive extraction followed by high-performance liquid chromatography-diode array detection." *Analytica Chimica Acta*, Jan. 2015, 855: 41-50.

Schirmer, C. et al., "Synthesis of a molecularly imprinted polymer for the selective solid-phase extraction of chloramphenicol from honey." *J Chromatogr A.*, Nov. 3, 2006, 1132(1-2): Abstract.

Shi, X. et al., "Molecularly imprinted polymer microspheres for solid-phase extraction of chloramphenicol residues in foods." *J Chromatogr B Analyt Technol Biomed Life Sci.*, May 1, 2007, 850(1-2): Abstract.

Tolika, EP et al., "Development and validation of an HPLC method for the determination of ten sulfonamide residues in milk according to 2002/657/EC." *J Sep Sci.*, Jul. 2011, 34(14): Abstract.

Turton, J.A. et al., "Studies on the haemotoxicity of chloramphenicol succinate in the Dunkin Hartley guinea pig." *Int. J. Exp. Path.*, 2002, 83: 225-238.

Yin, YM et al., "Dummy molecularly imprinted polymers on silica particles for selective solid-phase extraction of tetrabromobisphenol A from water samples." *J Chromatogr A*, Jan. 13, 2012, 1220: Abstract.

\* cited by examiner

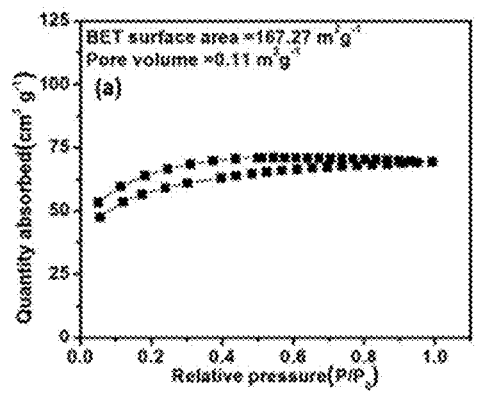 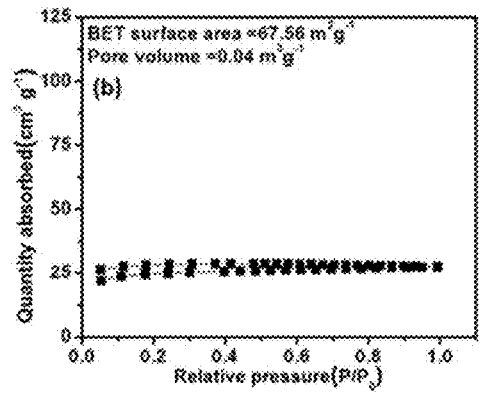
FIG. 4A    FIG. 4B
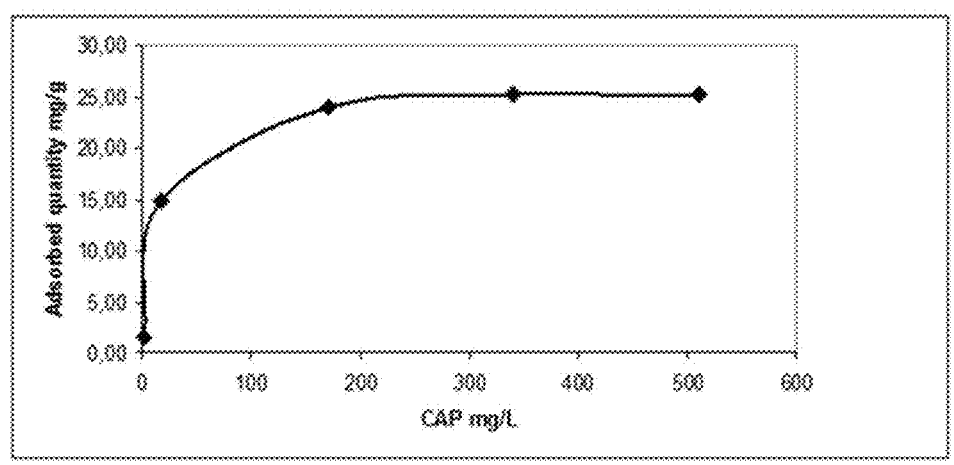
FIG. 5

MATERIALS AND METHODS FOR THE DETECTION OF TRACE AMOUNTS OF SUBSTANCES IN BIOLOGICAL AND ENVIRONMENTAL SAMPLES

CROSS-REFERENCE TO A RELATED APPLICATION

This application claims the benefit of U.S. provisional application Ser. No. 62/243,977, filed Oct. 20, 2015, which is incorporated herein by reference in its entirety.

BACKGROUND OF INVENTION

It is often necessary, for health and safety reasons, to detect small amounts of substances in biological and environmental samples. The detection of such substances would ideally be done with good sensitivity and specificity, easily, and at low cost. Such detection is often difficult, however, due to a variety of reasons, including the complexity of the samples that are being tested.

Chloramphenicol (CAP) is an antibiotic used for the treatment of bacterial infections, and it is often administered to animals for disease prevention (M. E. Falagas, A. P. Grammatikos, A. Michalopoulos, Potential of old-generation antibiotics to address current need for new antibiotics, Expert Review of Anti-Infective Therapy, 6 (2008) 593-600; J. A. Turton, C. M. Andrews, A. C. Havard, T. C. Williams, Studies on the haemotoxicity of chloramphenicol succinate in the Dunkin, Hartley guinea pig, International Journal of Experimental Pathology, 83 (2002) 225-238). CAP is a protein synthesis inhibitor that acts primarily by binding reversibly to the 50S ribosomal subunit and also can inhibit mitochondrial protein synthesis in mammalian cells. Therefore, despite its role in disease prevention and nonproliferation of bacterial growth, CAP is also associated with potentially serious toxic effects in humans, including bone marrow depression.

Moreover, antibiotic residues in animal milk may cause allergic reactions or lead to antimicrobial resistance. The use of CAP in food animals is, therefore, illegal in most countries, including the USA, Canada, China, and members of the European Union. However, the illicit use of CAP in cows to control mastitis and other animal diseases continues because of its low cost and easy availability (G. Y. Liu, C. Y. Chai, Towards the development of a sensitive electrochemical sensor for the determination of chloramphenicol residues in milk, Analytical Methods, 7 (2015) 1572-1577).

Analysis of ultra-trace level of contaminants, including CAP, in complex biological sample matrices is a daunting challenge due to the presence of numerous potential interferents in these samples.

Solid-phase extraction (SPE) is considered the gold standard among conventional sample preparation techniques, routinely used for the pre-concentration and clean-up of the target analyte(s) from complex sample matrices for subsequent analysis (B. Buszewski, M. Szultka, Past, Present, and Future of Solid Phase Extraction: A Review, Critical Reviews in Analytical Chemistry, 42 (2012) 198-213). However, conventional silica-based sorbents (e.g., C8, C18, etc.) do not offer adequate selectivity and specificity because the target analytes are predominantly retained on these sorbents by non-specific hydrophobic interactions, leading to simultaneous co-extraction of numerous endogenous interfering substances from the sample, thereby complicating the subsequent chromatographic analysis.

Molecularly imprinted polymers (MIPs) are synthetic polymeric materials that possess specific cavities complimentary to the shape, size, and functional groups of a template molecule used in the imprinting process (Techniques and Instrumentation in Analytical Chemistry, in: S. Börje (Ed.) Techniques and Instrumentation in Analytical Chemistry, Elsevier 2001, pp. ii; P. Manesiotis, L. Fitzhenry, G. Theodoridis, P. Jandera, 4.20—Applications of SPE-MIP in the Field of Food Analysis, in: J. Pawliszyn (Ed.) Comprehensive Sampling and Sample Preparation, Academic Press, Oxford, 2012, pp. 457-471; L. Chen, S. Xu, J. Li, Recent advances in molecular imprinting technology: current status, challenges and highlighted applications, Chemical Society Reviews, 40 (2011) 2922-2942).

Among many different synthesis pathways that can be used to create MIPs, the organic synthesis route appears to be the most popular (W. J. Cheong, S. H. Yang, F. Ali, Molecular imprinted polymers for separation science: A review of reviews, Journal of Separation Science, 36 (2013) 609-628). However, despite the advantages of organically synthesized MIPs, these materials often suffer from significant shortcomings, which include: (a) slow mass transfer kinetics; (b) heterogeneity of the binding sites; (c) low population of high-affinity binding sites; (d) irreversible shrinking and/or swelling when exposed to organic solvents, leading to considerable deformation of the imprinted cavities, and subsequent loss in template recognition capacity; (e) poor extraction performance when the sample matrices are aqueous or biological in nature and the target analytes are polar; (f) lack of ability to imprint thermal- and photosensitive template molecules due to the relatively high synthesis reaction temperature; (g) limited template removal option due to low thermal stability of organic polymers; and (h) low imprinting factor (IF) due to relatively high non-specific adsorption.

Some of these shortcomings of organic MIPs have been addressed by sol-gel synthesis approaches. Sol-gel synthesis of MIPs is versatile and possesses advantages including, for example, mild room temperature synthesis conditions, controllable pore size, high surface area, and tunable polarity of the matrix via manipulations in the sol-gel processing conditions such as, for example, the type and concentration of the precursors, catalysts, porogenic agents, and water content. The rigid, highly cross-linked structure of sol-gel MIPs possesses delicately imprinted sites with a high degree of selectivity compared to more flexible organic polymer MIPs.

Despite the potential of sol-gel organic-inorganic hybrid polymers as a host for efficient molecular imprinting, the advantages of these unique material systems have not been fully exploited. This is, in part, due to the lack of thorough understanding of sol-gel chemistry and the involvement of a large numbers of independent variables that eventually determine the ultimate physicochemical characteristics of the sol-gel materials. Irrational optimization of these variables often leads to sol-gel materials with poor accessibility to interaction sites, slow mass transfer rate, ineffective removal of the template, and low adsorption capacity.

Some researchers have proposed surface molecularly imprinted polymers (SMIP) using preformed silica particles as the imprinting host; however, due to the presence of a large number of residual surface silanol groups left on the silica substrate following the molecular imprinting, this approach often leads to high non-specific adsorption and results in low IF (J. Li, M. Yang, D. Huo, C. Hou, X. Li, G. Wang, D. Feng, Molecularly imprinted polymers on the surface of silica microspheres via sol-gel method for the selective extraction of streptomycin in aqueous samples, Journal of Separation Science, 36 (2013) 1142-1148; Y.-M. Yin, Y.-P. Chen, X.-F. Wang, Y. Liu, H.-L. Liu, M.-X. Xie, Dummy molecularly imprinted polymers on silica particles for selective solid-phase extraction of tetrabromobisphenol A from water samples, Journal of Chromatography A, 1220 (2012) 7-13; J.-H. Hu, T. Feng, W.-L. Li, H. Zhai, Y. Liu, L.-Y. Wang, C.-L. Hu, M.-X. Xie, Surface molecularly imprinted polymers with synthetic dummy template for simultaneously selective recognition of nine phthalate esters, Journal of Chromatography A, 1330 (2014) 6-13). As such, surface imprinting is not a viable solution for molecular imprinting if high IF, fast mass transfer kinetic, and high template adsorption capacity are desired.

Milk is a complicated sample matrix that requires multi-step sample preparation procedures. For the isolation of CAP in milk, various techniques have been proposed including liquid-liquid extraction (LLE) (X. Z. Shi, A. B. Wu, S. L. Zheng, R. X. Li, D. B. Zhang, Molecularly imprinted polymer microspheres for solid-phase extraction of chloramphenicol residues in foods, Journal of Chromatography B-Analytical Technologies in the Biomedical and Life Sciences, 850 (2007) 24-30), solid phase extraction (SPE) (R. S. Nicolich, E. Werneck-Barroso, M. A. S. Marques, Food safety evaluation: Detection and confirmation of chloramphenicol in milk by high performance liquid chromatography-tandem mass spectrometry, Analytica Chimica Acta, 565 (2006) 97-102; E. G. Karageorgou, V. F. Samanidou, Development and validation according to European Union Decision 2002/657/EC of an HPLC-DAD method for milk multi-residue analysis of penicillins and amphenicols based on dispersive extraction by QuEChERS in MSPD format, Journal of Separation Science, 34 (2011) 1893-1901; M. Ramos, A. Aranda, M. M. de Pozuelo, T. Reuvers, Chloramphenicol residues in food samples: Their analysis and stability during storage, Journal of Liquid Chromatography & Related Technologies, 26 (2003) 2535-2549), and fabric phase sorptive extraction (FPSE) (V. Samanidou, L. D. Galanopoulos, A. Kabir, K. G. Furton, Fast extraction of amphenicols residues from raw milk using novel fabric phase sorptive extraction followed by high-performance liquid chromatography-diode array detection, Analytica Chimica Acta, 855 (2015) 41-50). Deproteinization of milk is generally used prior to sample enrichment and clean-up by continuous solid phase extraction (D. R. Rezende, N. Fleury Filho, G. L. Rocha, Simultaneous determination of chloramphenicol and florfenicol in liquid milk, milk powder and bovine muscle by LC-MS/MS, Food Additives and Contaminants Part a—Chemistry Analysis Control Exposure & Risk Assessment, 29 (2012) 559-570).

The use of MIPs for the extraction and quantification of CAP in milk-based matrices has been suggested by Mohamed et al. in 2007 (R. Mohamed, J. Richoz-Payot, E. Gremaud, P. Mottier, E. Yilmaz, J. C. Tabet, P. A. Guy, Advantages of molecularly imprinted polymers LC-ESI-MS/MS for the selective extraction and quantification of chloramphenicol in milk-based matrixes. Comparison with a classical sample preparation, Analytical Chemistry, 79 (2007) 9557-9565). An improved method for trace analysis of CAP in honey, urine, milk and plasma using MIPs was proposed by Boyd et al., 2007 (B. Boyd, H. Bjork, J. Billing, O. Shimelis, S. Axelsson, M. Leonora, E. Yilmaz, Development of an improved method for trace analysis of chloramphenicol using molecularly imprinted polymers, Journal of Chromatography A, 1174 (2007) 63-71). The selective determination of CAP at trace levels in milk samples by an electrode modified with molecularly imprinted polymer has also been reported (T. Alizadeh, M. R. Ganjali, M. Zare, P. Norouzi, Selective determination of chloramphenicol at trace level in milk samples by the electrode modified with molecularly imprinted polymer, Food Chemistry, 130 (2012) 1108-1114). CAP was also identified in urine, feed water, milk and honey samples using molecular imprinted polymer clean-up by a commercially available MIPSPE column (Supel MIP) prior to GC/MS analysis after silylation of the antibiotic (M. Rejtharova, L. Rejthar, Determination of chloramphenicol in urine, feed water, milk, and honey samples using MIP clean-up, Journal of Chromatography A, 1216 (2009) 8246-8253). Although Supel MIP columns, presumably synthesized via an organic polymer approach, have demonstrated clear advantages over C18 SPE cartridges in extracting and pre-concentrating CAP from milk and other aqueous samples, due to the simultaneous extraction of non-specific matrix interferents from complex sample matrices, a series of washing steps had to be incorporated into the sample preparation regime followed by vacuum drying of the sorbent and subsequent elution of the analyte with larger volume of eluent.

As such, despite the inherent advantages over C18 SPE sorbent, the CAP imprinted Supel MIP method is labor-intensive, time-consuming and, contradictory to the principle of green analytical chemistry (GAC) (M. Farre, S. Perez, C. Goncalves, M. F. Alpendurada, D. Barcelo, Green analytical chemistry in the determination of organic pollutants in the aquatic environment, Trac-Trends in Analytical Chemistry, 29 (2010) 1347-1362; M. de la Guardia, Green analytical chemistry, Trac-Trends in Analytical Chemistry, 29 (2010) 577-577). Unavoidable application of solvent evaporation followed by sample reconstitution as an integral part of this sample preparation strategy often leads to irreversible analyte loss, poor data quality and low sample throughput.

No sol-gel derived CAP-imprinted sorbent material system has been reported for the separation and detection of this important analyte from milk or other biological samples.

BRIEF SUMMARY

The subject invention provides chemical compositions and synthesis strategies to create molecularly imprinted polymers (MIPs) via sol-gel processes. In a specific embodiment, the subject invention utilizes an organic, inorganic, or metallic target analyte to create a hybrid organic-inorganic or inorganic three-dimensional network possessing cavities complementary to the shape, size, and functional orientation of a target analyte. In some embodiments, the compositions of MIPs are obtained via a molarity-based approach. Advantageously, these cavities exhibit high affinity towards the target analyte, and its structural analogs, and remain indifferent to other molecules or species present in the same sample matrix.

In one embodiment, the subject invention provides a synthesis and post-synthesis processing strategy to effectively create cavities of a target analyte (e.g., molecules or ions) in a network comprising silica, zirconia, titania, germania, or a mixture thereof that demonstrate high affinity towards the template analyte, similar to antibody-antigen interactions. Advantageously, the sol-gel inorganic and/or hybrid organic-inorganic polymeric networks provided herein possess advanced material properties such as, for example, adjustable porosity, tunable selectivity, high thermal and solvent stability, and stability over a wide range of pH.

In exemplary embodiments, the formulations, the synthesis, and post-synthesis processing strategies provided herein were rigorously tested using chloramphenicol (CAP), a veterinary antibiotic as a model target analyte. The CAP-imprinted sol-gel inorganic-organic hybrid polymeric sorbents were found to be highly selective towards trace amounts of CAP and indifferent towards matrix interferents present in biological samples such as milk. Synthesis of other MIPs with environmental, pharmaceutical, chemical, clinical, toxicological, and national security implications can be conducted in accordance with teachings of the subject invention.

Advantageously, exemplary embodiments provide advanced sorbent material systems with predesigned cavities in a sol-gel hybrid organic-inorganic polymeric substrates for efficient extraction and/or pre-concentration of a variety of target analytes such as, for example, organic/inorganic molecules, organic/inorganic ions, and heavy metals from different sample matrices including, for example, forensic specimens; trace organic pollutants from environmental, food, beverage, pharmaceutical, and chemical samples; and drug or poison residues and metabolites thereof from biological samples.

BRIEF DESCRIPTION OF DRAWINGS

FIGS. 4A-4B show the BET adsorption isotherm graphs for (4A) sol-gel MIP and (4B) sol-gel NIP, respectively.

FIG. 5 shows the retention capacity of the sol-gel MIPSPE sorbent material.

DETAILED DISCLOSURE

Figure 1:
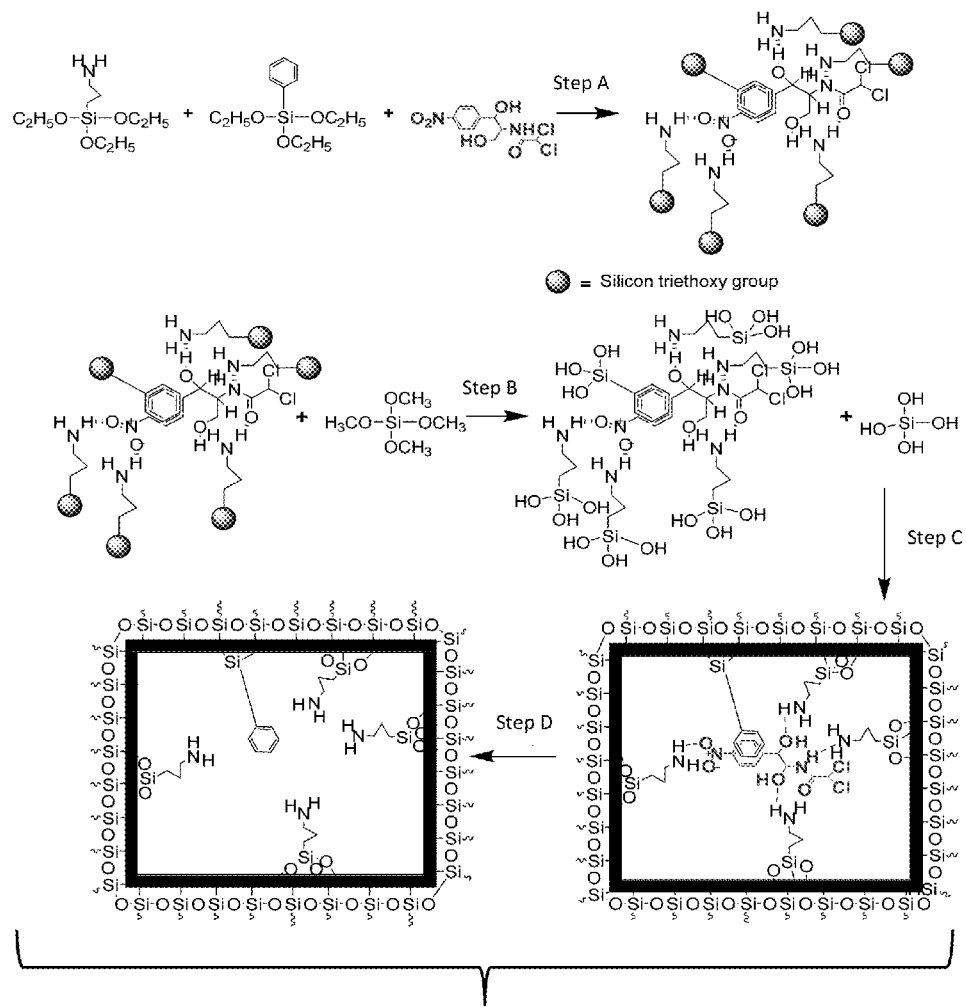
FIG. 1 shows the synthesis scheme of a chloramphenicol (CAP)-imprinted sol-gel MIP comprising the following steps: (A) complexation of 3-APTES and triethoxyphenylsilane with the CAP template; (B) acid-catalyzed hydrolysis of the sol-gel precursors; (C) condensation of hydrolyzed precursors to form a 3D sol-gel networks with the encapsulated templates; and (D) removal of the template from sol-gel 3D polymeric networks.
Figure 2A:
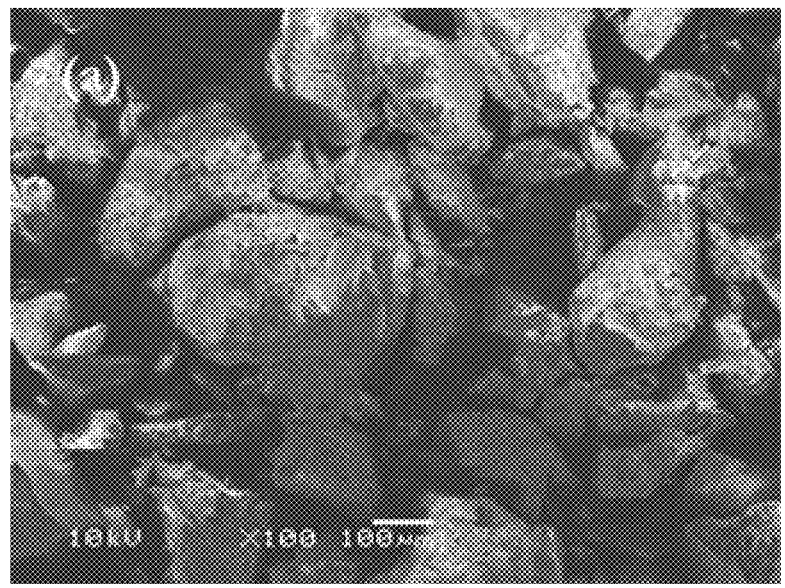
FIGS. 2A-2D show SEM images of CAP-imprinted sol-gel (MIP) at (2A) 100× and (2B) 500× magnification, and non-imprinted sol-gel (NIP) at (2C) 100× and (2D) 500× magnification.
Figure 2B:
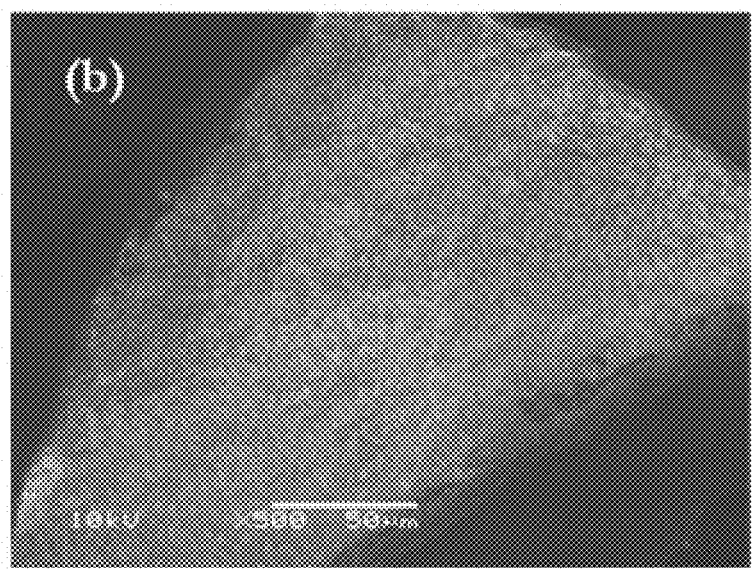
Figure 2C:
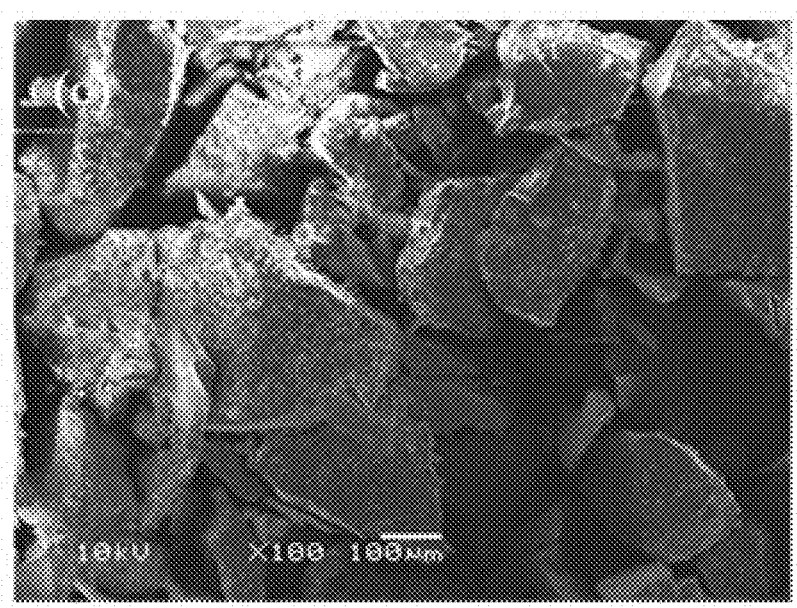
Figure 2D:
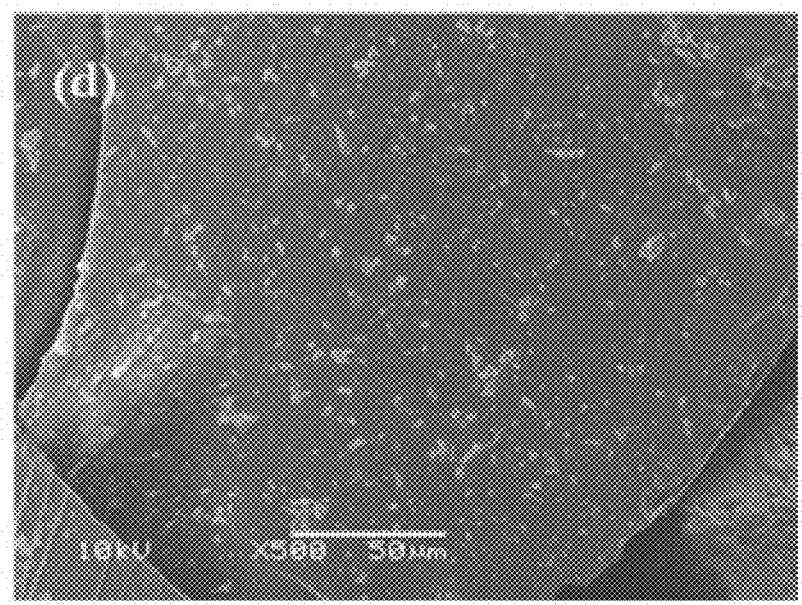

The subject invention provides chemical compositions and synthesis strategies to create molecularly imprinted polymers (MIPs) via sol-gel processes. In a specific embodiment, the subject invention utilizes an organic, inorganic, or metallic template analyte to create a hybrid organic-inorganic or inorganic three-dimensional network possessing cavities complementary to the shape, size, and functional orientation of the template molecule or ions. The subject invention further pertains to the use of the novel MIPs as selective solid phase extraction (SPE) sorbents for pre-concentration and clean-up of trace substances in biological and environmental samples. Synthesis of other molecularly imprinted polymers with environmental, pharmaceutical, chemical, clinical, toxicological, and national security implications can be conducted in accordance with the teachings of the subject invention.

The term "complementary" as used herein indicates that each molecular cavity left behind in the MIP matrix has a size matching that of the target analyte as well as binding site(s) with affinity towards chemical functional groups present in the analyte. In some embodiments, the target analyte can be eluted or extracted from the polymer matrix using a number of methods. In certain embodiments, the extraction can be done using an appropriate solvent such as, for example, methanol, ethanol, isopropanol, acetonitrile, formic acid, acetone, and combinations thereof. In further embodiments, the binding between the target analyte and its complementary molecular cavities is reversible.

In some embodiments, non-limiting examples of target analytes that can be imprinted in sol-gel MIP matrix provided herein include drugs, biological molecules (e.g., cells, proteins, and amino acids), toxins, viruses, and structural analogues thereof.

In some embodiments, the target analyte is an antibiotic selected from chloramphenicol (CAP), thiamphnicol, florfenicol, ceftiofur, cefaclor, oxytetracycline, tetracycline, sulfamethazine, sulfadimethoxine, amoxicillin, ampicillin, ciprofloxacin, enrofloxacin, and structural analogues thereof. In an exemplary embodiment, the target analyte is CAP.

In some embodiments, the subject invention provides facile synthesis and post-synthesis processing strategies to create cavities of a template molecule or template ion on a network comprising silica, zirconia, titania, and/or germania, or a mixture thereof that demonstrates high affinity towards the target analyte. Advantageously, the sol-gel inorganic and/or hybrid organic-inorganic polymeric networks provided herein possess advanced material properties such as, for example, adjustable porosity, tunable selectivity, high thermal and solvent stability, and stability over a wide range of pH.

Specifically exemplified herein is the detection of CAP from milk samples and the subsequent separation and quantification thereof using high-performance liquid chromatography (HPLC) equipped with ultra-violet (UV) and/or mass spectrometry (MS) detection. Non-limiting examples of other samples that may comprise CAP include blood, plasma, serum, and urine.

In a specific embodiment, an MIP imprinted with CAP is synthesized via a sol-gel matrix imprinting approach by employing triethoxyphenylsilane (TEPS) and 3-aminopropyltriethoxysilane (3-APTES) as sol-gel functional precursors, tetramethyl orthosilicate (TMOS) as the cross-linking precursor, water as the hydrolytic agent, HCl as the catalyst, and isopropanol as the polymerization solvent, resulting in a hybrid inorganic-organic 3D network.

As described herein, both the sol-gel MIP and sol-gel non-imprinted polymer (NIP) have been synthesized and characterized using different techniques such as, for example, scanning electron microscopy (SEM), Fourier-transform infra-red spectroscopy (FT-IR), and nitrogen adsorption porosimetry. Those skilled in the art would recognize that other characterization techniques now known or hereafter developed can also be used to analyze the MIPs and NIPs networks provided herein.

The MIPs synthesized using compositions and methods provided by the subject invention have many advantages. For example, simultaneous exploitation of two functional precursors in the molecular imprinting process results in a high imprinting factor (IF). In an exemplary embodiment, the IF for CAP-imprinted MIP is approximately 9.7. Relatively low IFs for other analogous compounds indicate a high degree of selectivity of molecular cavities for CAP. Advantageously, these cavities exhibit high affinity towards the target analyte, or its structural analogs, and simultaneously remain indifferent, or chemically inert and unreactive, toward other molecules or species present in the same sample matrix.

In an exemplary embodiment, the sol-gel MIP sorbent provided herein demonstrates good extraction and pre-concentration performance for isolating CAP from milk and can be used up to, for example, two, three, four, five, or six times without significantly losing its extraction capacity. The synthesized sol-gel MIP also exhibited low cross reactivity with antibiotics of other classes. The method was validated according to the EU criteria for confirmatory analytical methods. Advantageously, this highly efficient sol-gel MIP can be routinely used in testing laboratories to ensure food quality and consumer safety for the trace analysis of CAP in milk samples. It is an advantageous feature of the subject invention that the CAP-imprinted MIP is indifferent towards other matrix interferents present in samples such as, for example, milk, highlighting the sensitivity and selectivity of the sol-gel MIP matrix provided herein.

In the sol-gel matrix imprinting process exemplified herein, CAP was used as the template molecule, 3-aminopropyltriethoxysilane and triethoxyphenylsilane as the functional precursors, tetramethyl orthosilicate as the cross-linker, isopropanol as the solvent/porogen, and HCl as the sol-gel catalyst. By comparison, sol-gel NIP was also synthesized under identical conditions in the absence of the template molecules. Both the sol-gel MIP and sol-gel NIP were subjected to physicochemical characterization by scanning electron microscopy (SEM), Fourier transform infrared spectroscopy (FT-IR), and nitrogen adsorption porosimetry. Characterization results demonstrated significant structural and morphological differences between sol-gel MIP and sol-gel NIP sorbents, thus confirming the effectiveness of the sol-gel MIP matrix and the synthesis methods thereof as provided herein.

In some embodiments, the synthesized sol-gel MIP and sol-gel NIP were evaluated as sorbents for molecularly imprinted solid-phase extraction (MISPE) of CAP in milk samples. The effect of critical solid-phase extraction parameters such as flow rate, nature of the eluent, sample and eluent volume, selectivity coefficient, and retention capacity were studied with regards to the retention and desorption of CAP to the CAP-imprinted sol-gel MIP sorbent.

In some embodiments, the subject invention provides an apparatus in which a sol-gel sorbent material (e.g., the CAP-imprinted sol-gel MIP) can be stored and a sample of interest (e.g., milk) can be subsequently passed through to allow the extraction of a target analyte. In an exemplary embodiment, the apparatus is a syringe equipped with, for example, a barrel for storing the sorbent material and a plunger to push a sample through the sorbent. Alternatively, the apparatus can be a solid-phase extraction cartridge.

Competition and cross reactivity tests demonstrated that the sol-gel MIP sorbent possesses significantly higher specific retention and enrichment capacity for CAP compared to its non-imprinted analogue. The maximum imprinting factor (IF) was found to be 9.7, and the highest adsorption capacity of CAP by the sol-gel MIP was determined to be 23 mg/g. The sol-gel MIP was found to be sufficiently selective towards CAP to provide the necessary maximum required performance limit (MRPL) of 0.3 µg/kg for CAP as set forth by European Commission when LC-MS was deployed as the analytical instrument.

Advantageously, exemplary embodiments of the subject invention provide advanced sorbent material systems with predesigned cavities in sol-gel hybrid organic-inorganic polymeric substrates for efficient extraction and/or pre-concentration of a variety of target analytes such as, for example, organic/inorganic molecules, organic/inorganic ions, and heavy metals from different sample matrices including, for example, forensic specimens; trace organic pollutants from environmental, food, beverage, pharmaceutical, and chemical samples; and drug or poison residues and metabolites thereof from biological samples.

EXAMPLES

Following are examples which illustrate procedures for practicing the invention. These examples should not be construed as limiting. All percentages are by weight and all solvent mixture proportions are by volume unless otherwise noted.

Chloramphenicol (CAP) was purchased from Alfa-Aesar (Karlsruhe, Germany). thiamphenicol (TAP) and florfenicol (FFC) were purchased from Sigma-Aldrich (St. Louis, Mo., USA). HPLC grade methanol and acetonitrile were obtained from Fisher Scientific (Steinheim, UK), isopropanol (2-propanol) was supplied by Panreac (Barcelona, Spain). Acetone (p.a.) was supplied by Chem-Lab NV (Zedelgem, Belgium). HPLC grade water by Merck (Darmstadt, Germany) was used in mobile phase preparation, while high purity water, obtained by a Milli-Q purification system (Millipore, Bedford, Mass., USA), was used throughout the following examples. Formic acid (99-100%) was obtained from Chem-Lab and acetic acid glacial (100%) was purchased from Merck.

Additional antibiotics used for cross reactivity studies included sulfamethazine, sulfadimethoxine, cefaclor, ceftiofur, amoxicillin, ampicillin and ciprofloxacin, which were purchased from Sigma-Aldrich (St. Louis, Mo., USA). Enrofloxacin, tetracycline and oxytetracycline were purchased from Fluka Chemie (Buchs, Belgium).

Milk samples were collected from local food stores. Different varieties of fresh milk were analysed: (a) skim milk (0% fat), (b) semi-skim milk (1.5% fat), and (c) full-fat milk (3.5% fat). All milk samples were refrigerated at 4° C.

Example 1—Preparation of Sol-Gel MIP and Sol-Gel NIP

Preparation of Chloramphenicol Complex with Functional Precursors

The synthesis scheme of CAP imprinted sol-gel MIP is shown in FIG. 1. The self-assembled complex between the CAP template and the sol-gel precursors, 3-APTES and TEPS were obtained by vigorously mixing 250 mg of CAP, 0.8 g of 3-APTES, 0.8 g of TEPS, and 4 mL of isopropanol together followed by sonication for 30 min. The mixture was incubated at room temperature for 6 hr so that a 3D complex with distinct stereo-chemical orientation between the template and the sol-gel precursors forms via hydrogen bonding.

The schematic process presented in FIG. 1 comprises four steps, including (a) complexation of sol-gel functional precursors (e.g., 3-APTES and TEPS) with CAP template; (b)

acid-catalyzed hydrolysis of crosslinking sol-gel precursor; (c) simultaneous hydrolysis of functional precursors and condensation of hydrolyzed precursors to form a 3D sol-gel network with encapsulated template analyte; and (d) removal of the template from the sol-gel 3D polymeric network.

Due to the presence of a benzene ring as well as a large number of hydrogen bond donors and acceptors in CAP, TEPS (to provide μ-μ interaction), and 3-APTES (to provide hydrogen bonding interaction) were chosen.

During the complexation, both of the sol-gel precursors positioned themselves around the template utilizing their specific interaction capability. As such, a template-precursors complex was formed with a distinct 3D stereo-chemical orientation of the participating entities. To ensure uninterrupted interactions between the template and precursors, isopropanol, a relatively nonpolar solvent, was used as the reaction medium.

Another important task in sol-gel MIP synthesis is to obtain complete hydrolysis of the crosslinking sol-gel precursors in order to ensure successful integration of the template complex into the 3D sol-gel network. Complete hydrolysis of the methoxy functional groups into hydroxyl functional groups was ensured by dissolving TMOS in an appropriate volume of solvent/porogen isopropanol and reacting with water in the presence of HCl as a catalyst for a prolonged period of time under elevated temperature.

Hydrolysis of the Crosslinking Agent

To initiate the hydrolysis of the crosslinking agent, 2.5 mL of TMOS was added to 20 mL of isopropanol and the mixture was thoroughly mixed by vortexing for 5 min. Subsequently, 750 μL of 0.1 M HCl was added to the mixture and kept in a silicone oil bath at 50° C. for 12 hr to ensure complete hydrolysis of the sol-gel precursor.

Sol-Gel Condensation to Form 3D Molecularly Imprinted Polymer (MIP) Network

The complex mixture containing the template was then added to the hydrolyzed solution of the cross-linking reagent and was vortexed for another 5 min. The sol solution comprising the CAP template was kept at 50° C. in the silicone oil bath for 4 hr to form a transparent gel mixture, followed by another 24 hr at the same temperature for aging and ripening of the network.

When the template-precursors complex is added to the sol solution containing the hydrolyzed crosslinking agent, simultaneous hydrolysis and condensation of the functional precursors as well as the condensation of the hydrolyzed crosslinking agent began in the presence of the acid catalyst HCl and at an elevated reaction temperature. Soon, a 3D network of sol-gel polymeric network with entrapped template and solvent/porogen self-assembled.

Removal of the Template from Sol-Gel MIP Sorbent

Following the preparation of sol-gel MIP sorbent, the template (CAP) was removed from the polymer networks so that the imprinted cavities complimentary to the size, shape, and functionality of the template molecules were left behind throughout the matrix. Experiments showed that methanol (MeOH) was suitable for the removal of CAP from the sol-gel MIP sorbent after 10 cycles of sonication with 10 mL of MeOH for 30 min. Alternatively, 10 times of centrifugation for 30 min with 10 mL MeOH at 1900 g may be used for the exhaustive removal of the template. Solvent mediated template removal continued until the washing solution became free of CAP, which was confirmed by HPLC analysis.

The template-free particulates were then dried in an oven at 50° C. for 30 min. Non-imprinted sol-gel polymer sorbent (sol-gel NIP) was prepared following the same procedures established herein in the absence of the CAP template.

Aging and ripening of the sol-gel network for a prolonged period of time ensures that condensation has completed and as a result, the subsequent removal of the solvent and the template analyte from the sol-gel network would not disturb its structural and morphological integrity.

Example 2—Characterization of Sol-Gel MIP and Sol-Gel NIP: SEM

The CAP-imprinted sol-gel MIP sorbent as well as the NIP control sample were characterized using scanning electron microscopy (SEM). The SEM images are presented in FIGS. 2A-2D.

The surface morphology of both the imprinted and non-imprinted particulates appeared to be identical at lower magnification (100×); however, at higher magnification (500×), the imprinted surface demonstrates a sponge-like, porous, and roughened surface morphology, while the non-imprinted control shows a smooth, glassy surface at the same magnification.

Example 3—Characterization of Sol-Gel MIP and Sol-Gel NIP: FT-IR

Figure 3A:
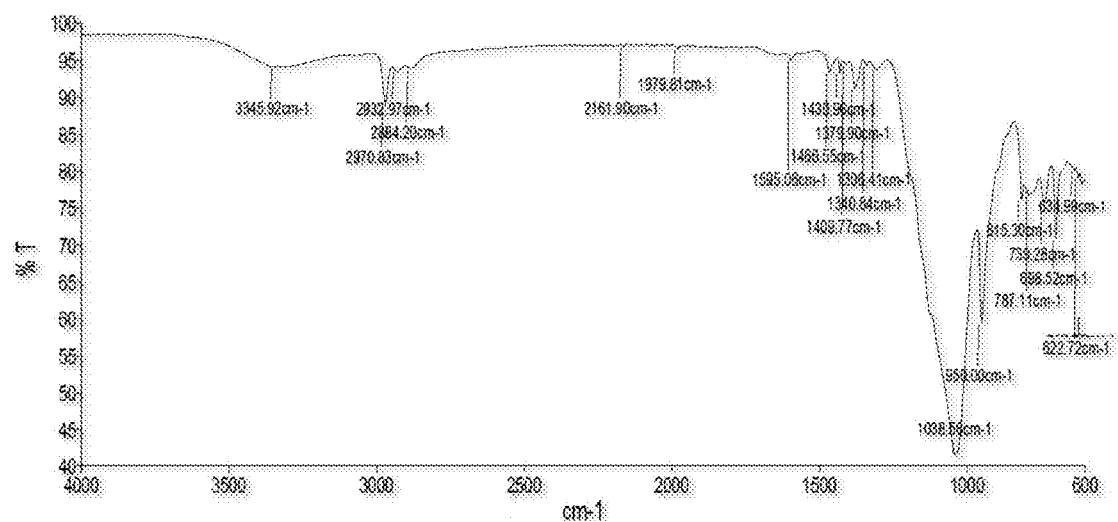
FIGS. 3A-3C show the FT-IR spectrum of (3A) sol-gel MIP, (3B) sol-gel NIP, and (3C) a CAP template molecule, respectively.
Figure 3B:
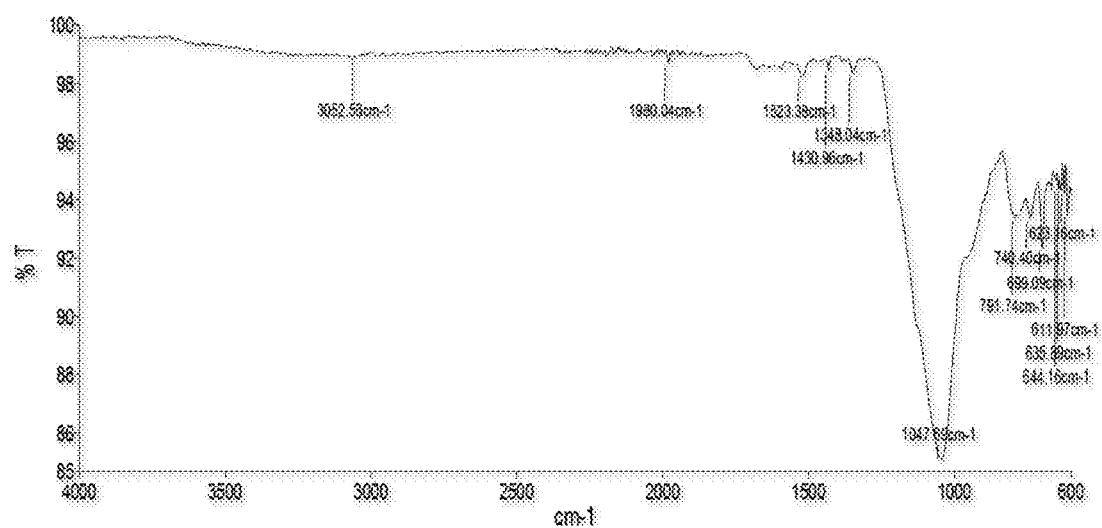
Figure 3C:
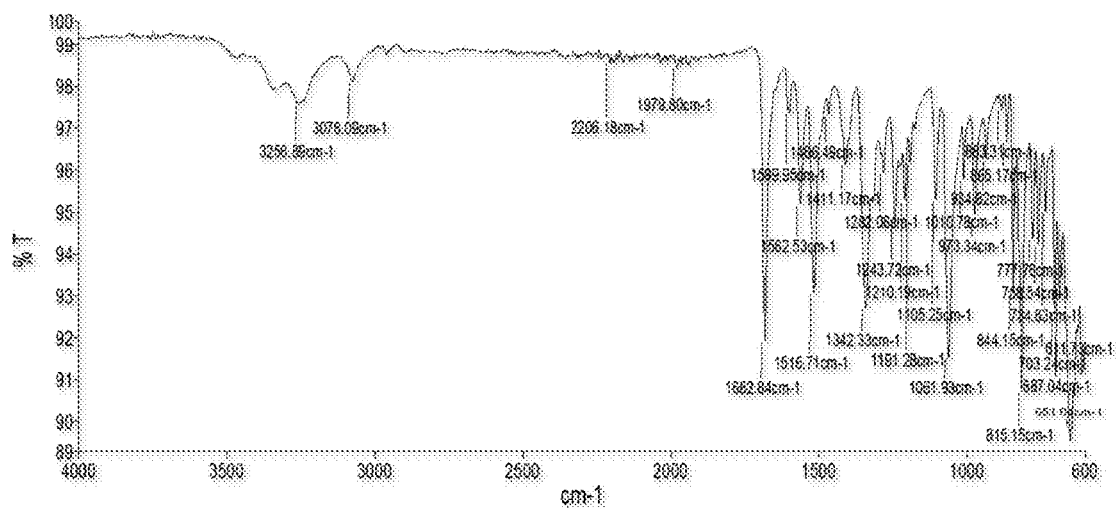

To study the presence of various functional groups and the chemical linkages within the sol-gel MIP and sol-gel NMIP sorbents, Fourier transform infra-red spectroscopy (FT-IR) was employed. FIGS. 3A-3C show the FT-IR spectrum of (a) the sol-gel MIP, (b) the sol-gel NIP, and (c) the CAP template, respectively.

The spectral features observed in FIGS. 3A and 3B around 1038-1047 $cm^{-1}$ were attributed to Si—O—Si stretching vibrations. The bands around 787-792 $cm^{-1}$ represent Si—O vibrations. The bands around 1595 $cm^{-1}$ are resulted from nitro phenyl group of the sol-gel precursor, 3-APTES. Bands at 698 $cm^{-1}$ and 739 $cm^{-1}$ were attributed to another sol-gel precursor, TEPS.

The absence of any features of CAP as shown in FIG. 3C in both the sol-gel MIP and sol-gel NIP strongly suggests the successful quantitative removal of the template molecules from the sol-gel MIP.

Example 4—Characterization of Sol-Gel MIP and Sol-Gel NIP: HPLC-UV

An LC-10AD pump by Shimadzu (Kyoto, Japan) was used to deliver the mobile phase to the analytical column. The sample was injected via a Rheodyne 7125 injection valve (Rheodyne, Cotati, Calif., USA). UV Detection was achieved at a sensitivity setting of 0.0005 AUFS using an SSI 500 UV-vis detector (SSI, State College, Pa., USA).

Milli-Q water, included in the mobile phase, was filtered using a glass vacuum-filtration apparatus obtained from Alltech Associates, (Deerfield, Ill., USA) and Whatman Cellulose Nitrate 0.2 mm—WCN Type (47 mm DIA) membrane filters (Whatman Laboratory Division, Maidstone, England). Degassing of solvents was achieved by helium sparging prior to use.

Sonication was performed by an ultrasonic bath Transonic 460/H (35 kHz, 170 W, Elma, Germany) and centrifugations were carried out using a Hermle centrifuge, model Z-230 (B. Hermle, Gosheim, Germany). A Visiprep™ SPE vacuum manifold by Supelco (Bellefonte, Pa., U.S.A.), a nine port Reacti-Vap™ (model 18780) by PIERCE (Rockford, Ill., USA) were used.

A PerfectSil 120 ODS-2 analytical column (250 mm×4.0 mm, 5 μm) by MZAnalysenTecnhik (Mainz, Germany) was used for the separation at ambient temperature. The mobile phase consisted of acetonitrile-water (30:70%, v/v) and was delivered isocratically at a flow rate of 1.0 mL/min. Aliquots of 20 μL were injected. Monitoring and quantitation of CAP was performed at 280 nm.

Example 5—Characterization of Sol-Gel MIP and Sol-Gel NIP: LC-MS

LC-MS analysis was performed using a Shimadzu LCMS-2020 (Kyoto, Japan) mass spectrometer. Standard LC-20AD dual pistons and pumps with high-pressure mixing provided flow (0.5 mL/min) for the interface and the detector. Samples were injected (50 μL volume) by a Shimadzu SIL-20AC HT autosampler, which operated for both flow and column injection analysis. The LC-MS-2020 was operating in the negative ionization SCAN and the selected ion monitoring (SIM) modes. Scans were made from 50-500 at 0.5-s intervals (scan speed=1500 amu/s). Initially, the main (−) m/z ion for each analyte in the scan method was chosen and then the analysis was repeated at the SIM mode and its response ions was measured. The results were verified by triplicate measurements.

The sample solution was drawn into a capillary pipe with a high voltage of −3.5 kV applied. Nebulizer gas was blown out around the outside of the capillary pipe, spraying the solution and generating fine droplets electrostatically charged with the same sign as the applied voltage. Interface temperature was maintained at 350° C. After being sprayed and ionized by the ionization probe, the sample passed through the sample introduction line (Desolvation Line-DL) oriented at 250° to the spray, into the first stage primary vacuum chamber (lens system). Excess solvent was expelled through the drainage port.

The temperature and voltage of the curved desolvation line (the inlet for the high vacuum region) were set at 250° C. and 0 V, while the nitrogen nebulizer gas flow remained constant at 1.5 L/min, respectively. Drying gas flow was set at 15 L/min. CAP was identified in negative scan mode at m/z=321. Mobile phase in LC-MS analysis was MeOH—$H_2O$ (at v/v of 40:60). Methanol was chosen as the mobile phase due to its ability to provide higher signal than acetonitrile-water mixture.

Example 6—Characterization of Sol-Gel MIP and Sol-Gel NIP: Nitrogen Adsorption Porosimetry The textural characteristics of sol-gel MIP and sol-gel NIP particles were investigated using nitrogen adsorption/desorption isotherm.

The BET adsorption isotherm graphs for sol-gel MIP and sol-gen NIP are presented in FIGS. 4A and 4B. The adsorption data are presented in Table 1 below.

TABLE 1

BET surface area ($m^2/g$), pore volume, and average pore diameter of CAP-imprinted sol-gel polymer and corresponding sol-gel non-imprinted polymer.

| Polymer | BET surface area ($m^2 \cdot g^{-1}$) | Pore volume ($cm^3 \cdot g^{-1}$) | Average pore diameter (Å) |
|---|---|---|---|
| Sol-gel MIP | 167.3 | 0.1075 | 25.7 |
| Sol-gel NMIP | 67.6 | 0.0424 | 25.1 |

The specific surface area and the pore volume of the sol-gel MIP and the sol-gel NIP were significantly different from each other. The high specific surface area and larger pore volume of sol-gel MIP were good indicators of the relatively open 3D sol-gel network imparted by the presence of the self-assembled complex of the sol-gel precursors around the template molecules in a rigid stereo-chemical orientation. However, the average pore diameter of both imprinted and non-imprinted materials are similar, suggesting that the presence of porogen (e.g., isopropanol), and not the template, in the sol solution contributed primarily to the pores of the sol-gel polymeric network.

The specific surface area of the sol-gel MIP was calculated to be 167.3 $m^2/g$, which was significantly higher than that of both commercial silica (20 $m^2/g$) (W. Chen, Z. Fan, A. Dhanabalan, C. Chen, C. Wang, Mesoporous Silicon Anodes Prepared by Magnesiothermic Reduction for Lithium Ion Batteries, Journal of The Electrochemical Society, 158 (2011) A1055-A1059) and the sol-gel NIP. Both the sol-gel MIP and sol-gel NIP possess mesopores that allowed fast diffusion of the aqueous sample through the sol-gel sorbent matrix to achieve extraction equilibrium in a relatively short period of time.

Example 7—Evaluation of the Performance of MIPs: Enrichment Factor

The enrichment factor is a vital parameter in evaluating the extraction efficiency. The enrichment factor (EF) is calculated to be:

$$EF = V_{sample}/V_{eluent} = 10 \text{ mL}/0.5 \text{ mL} = 20$$

where $V_{sample}$ is the volume of the sample and $V_{eluent}$ is the volume of eluent solvent. In case of evaporation and reconstitution to 100 μL, the EF was 100.

Example 8—Evaluation of the Performance of MIPs: Retention Capacity of the Cap-Imprinted Sol-Gel Sorbent To determine the retention capacity (or sorption capacity) of the sol-gel derived CAP-imprinted polymer (maximum amount of the template retained by 1 g of MIP), 30 mg of polymer were saturated with CAP by passing several 5.0 mL aliquots of 100 mg/L CAP solution. After measuring the CAP content in elutes by HPLC, the retention capacity of the polymer was calculated to be 23 mg/g, as shown in FIG. 5.

Example 9—Evaluation of the Performance of MIPs: Selectivity of Cap Imprinted Sol-Gel Sorbent To establish the selectivity of a sol-gel MIP for a particular analyte, a non-imprinted polymer (sol-gel NIP) is synthesized in the same way as sol-gel MIP but in the absence of the template.

The IF reflects the tendency of the MIP to selectively recognize and bind the template. Competitive adsorption of MIP and NIP for CAP was investigated in a MIPSPE column system. The IF and the selectivity coefficient (SC) are indicators of the adsorption affinity of recognition sites to the imprinted CAP.

Selectivity Studies

The selectivity of sol-gel MIP particles for CAP was studied. For this purpose, 30 mg of sol-gel MIP or sol-gel NIP particles were packed in SPE cartridges. Aqueous sample solutions containing 10 ng/mL CAP was passed through the SPE cartridges holding imprinted or non-imprinted particles at a flow rate of 1 mL/min by the aid of a vacuum system. Elution of the extracted chloramphenicol was performed using methanol and the concentration of chloramphenicol was determined by the HPLC-UV method.

Imprinting factor (IF) of sol-gel MIP particles was determined by the following equation:

$$IF = K_{mip}/K_{nip}$$

where $K_{mip}$ and $K_{nip}$ are the partition coefficient of analyte for sol-gel MIP and sol-gel NIP, respectively, which are determined by $K = C_b/C_u$ where $C_b$ is the amount of CAP bound by the sol-gel MIP or sol-gel NIP and $C_u$ is the concentration of free chloramphenicol that remained in the solution.

Selectivity coefficient (SC) was calculated by the following equation:

$$SC = IF_{CAP}/IF_{other\_analyte}$$

Cross reactivity of sol-gel MIP towards other antibiotics was studied using several antibiotics of similar structure such as, for example, thiamphnicol and florfenicol, as well as other antibiotics with different structure and functional groups such as, for example, ceftiofur, cefaclor, oxytetracycline, tetracycline, sulfamethazine, sulfadimethoxine, amoxicillin, ampicillin, ciprofloxacin, and enrofloxacin. The binding efficiency was evaluated and was found to be less than 5% for the other antibiotics, thus indicating the high specificity of the prepared sol-gel MIP.

Specifically, Table 2 and Table 3 summarize the IF and SC values for CAP compared to its analogues when extraction was carried out from untreated raw milk and protein precipitated milk, respectively.

TABLE 2

Imprinting factors and selectivity coefficients for CAP and its analogues.

| Analyte | Imprinting Factor (IF) | Selectivity Coefficient (SC) |
|---|---|---|
| CAP | 5 | — |
| THF | 1.9 | 2.6 |
| FFC | 1.8 | 2.8 |

TABLE 3

Effect of protein precipitation agent to the IF of sol-gel MIP

| Protein precipitation agent | Recovery | IF |
|---|---|---|
| Acetonitrile, ACN | 22.8 | 1.83 |
| Formic acid, HCOOH 25% | 9.8 | 9.7 |
| Acetic Acid, CH$_3$COOH 25% | 2.6 | 1.75 |

An imprinting factor of 9.8 was measured for the CAP-MIP relative to the corresponding NIP when extraction was carried out from protein precipitated milk sample. This signifies a strong selective binding in the imprinted sites of the MIP for CAP. An imprinting factor of 5.0 was obtained when CAP was extracted from untreated milk. The discrepancy in the imprinting factor values can be explained by the fact that untreated milk is a colloidal system containing protein, fat, lipid, and other nano-size particles that may block the imprinted cavities, resulting in lower imprinting factors.

An imprinting factor of 1.9 and 1.8 was noticed for CAP analogues such as other amphenicols, namely thiamphenicol and florfenicol, respectively. The large difference in the IF for the template and its close structural analogs reflects the excellent specificity of the sol-gel MIP towards CAP. The typical imprinting factor reported in organically synthesized MIPs are in the range of 1-2 (J. Li, M. Yang, D. Huo, C. Hou, X. Li, G. Wang, D. Feng, Molecularly imprinted polymers on the surface of silica microspheres via sol-gel method for the selective extraction of streptomycin in aqueous samples, Journal of Separation Science, 36 (2013) 1142-1148; Y.-M. Yin, Y.-P. Chen, X.-F. Wang, Y. Liu, H.-L. Liu, M.-X. Xie, Dummy molecularly imprinted polymers on silica particles for selective solid-phase extraction of tetrabromobisphenol A from water samples, Journal of Chromatography A, 1220 (2012) 7-13; J.-H. Hu, T. Feng, W.-L. Li, H. Zhai, Y. Liu, L.-Y. Wang, C.-L. Hu, M.-X. Xie, Surface molecularly imprinted polymers with synthetic dummy template for simultaneously selective recognition of nine phthalate esters, Journal of Chromatography A, 1330 (2014) 6-13).

Example 10—Evaluation of the Performance of MIPs: Regeneration and Reusability of MIP The reusability is one of the key factors in novel sorbent applications and is favored by green analytical chemistry (GAC).

To show the reusability of CAP imprinted sol-gel MIP adsorbents, the adsorption-desorption cycle of CAP was repeated several times consecutively by using the same sorbent. No substantial decrease in the adsorption capacity of sol-gel MIP was observed up to six repeated usage, while a 12.5% reduction was found after the 7th cycle of consecutive use.

Example 11—Evaluation of the Performance of MIPs: Optimization of Adsorption-Desorption Studies Studies were carried out to investigate the influence of different parameters on the retention and desorption of CAP from MIP sorbent.

Effect of Type, Volume and Flow Rate on the Elution of CAP from MIP

Extraction columns using sol-gel-MIP and sol-gel NIP sorbents were prepared by packing the dried sol-gel MIP particles (30 mg) in 5 mL empty syringe barrels. Each barrel was attached with a stop cock and two frits were placed to the bottom and the top end of the MIP packed particles. The frits were obtained from commercial SPE cartridges. The MISPE columns were conditioned with 2 mL methanol and 2 mL of DI water, respectively, before loading the samples.

After loading, the samples were allowed to stay for 15 min before passing through the syringe barrel. Sample holding time was optimized after checking the extraction results by using 5 min, 10 min, 15 min, and 20 min of holding time, respectively.

The effect of the nature of eluent solvent was studied for the desorption of CAP from MIP sorbent. Elution of CAP was performed using seven different eluent systems including: acetonitrile, acetone, ethanol, methanol, 2-propanol, MeOH-ACN at v/v=1:1, and 10% formic acid.

Figure 6:
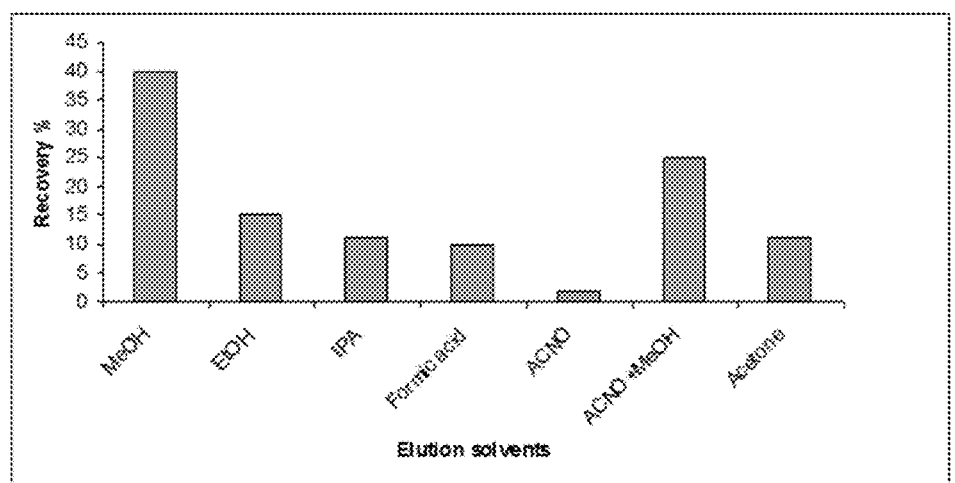
FIG. 6 shows the effect of different elution solvents on the percentage recovery of CAP from its sol-gel MIP.

As shown in FIG. 6, the use of MeOH yielded the highest percentage of recovery. In all solvents examined, the binding of CAP to the MIP was significantly higher than to the NIP, confirming the higher affinity of the imprinted polymer towards CAP.

Flow rate of sample solution and eluent solvent (0.5-2 mL/min) as well as the eluent volume (0.5-2 mL) were studied. The optimum volume of the eluent was 500 μL of methanol at a flow rate of 1 mL/min.

In order to study the effect of sample volume, aliquots of 0.5 g, 2 g, 5 g, and 10 g of milk, respectively, were studied. No matrix effect was observed in milk samples of up to 10 g.

Effect of Equilibrium Time

Figure 7:
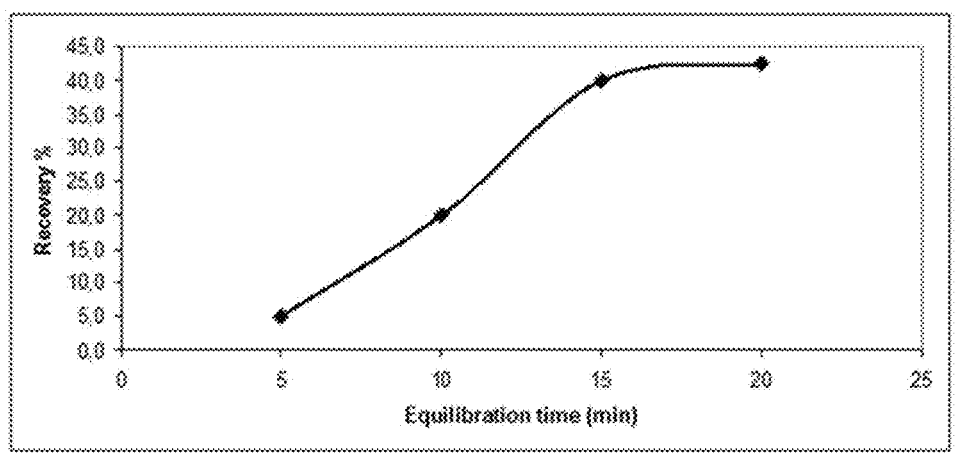
FIG. 7 shows the adsorption kinetic of CAP on the MIPSPE sorbent material.

Each sample was allowed to interact with the sol-gel MIP before passing through the column. Different equilibrium times, e.g., 5 min, 10 min, 15 min, and 20 min were tested and then the sample was passed at a flow rate of 1 mL/min. Fifteen minutes of equilibrium time yielded the highest extent of recovery as shown in FIG. 7.

Fat and Protein Removal from Milk Samples Prior to Solid Phase Extraction (SPE)

Since fat and proteins were expected to interfere with the binding sites and potentially deteriorate the performance of the sol-gel MIP, they were removed from each milk sample prior to being passed through the MIPSPE column.

For fat removal, milk samples were centrifuged while for protein precipitation different agents were investigated. Acetonitrile yielded the highest percentage of recovery, though formic acid gave the best IF as shown in Table 3.

Chromatograms representing extraction from blank matrices showed no interference due to the endogenous milk components, thus proving the superior selectivity of the method towards the target analyte and the absence of non-specific interactions, a common phenomenon that frequently inhibits the performance of organically synthesized MIPs.

Example 12—Method Validation and Analytical Performance

After establishing the optimal conditions for the extraction of CAP from the sol-gel MIP, the method for determining the concentration of CAP in milk samples was validated in terms of linearity, sensitivity, precision, accuracy, and applicability to real samples.

Preparation of Standard Solutions and Treatment of Milk Samples for Fat and Protein Removal Stock solution of CAP (100 mg/L) was prepared in water and, when kept at 4° C., was found stable for at least 3 months. Working standard solutions (0.05-20 ng/μL) were also prepared in water and were stable for the same period of time when refrigerated. Methanolic standard solutions of CAP were used in LC-MS analysis as the signal was seen to have been enhanced. Stock solutions of other antibiotics as well as chromatographic conditions for their analysis were prepared and analyzed following standard procedures recognized in the art (E. G. Karageorgou, V. F. Samanidou, Development and validation according to European Union Decision 2002/657/EC of an HPLC-DAD method for milk multi-residue analysis of penicillins and amphenicols based on dispersive extraction by QuEChERS in MSPD format, Journal of Separation Science, 34 (2011) 1893-1901; E. P. Tolika, V. F. Samanidou, I. N. Papadoyannis, Development and validation of an HPLC method for the determination of ten sulfonamide residues in milk according to 2002/657/EC, Journal of Separation Science, 34 (2011) 1627-1635; E. G. Karageorgou, V. F. Samanidou, I. N. Papadoyannis, Ultrasound-assisted matrix solid phase dispersive extraction for the simultaneous analysis of ss-lactams (four penicillins and eight cephalosporins) in milk by high performance liquid chromatography with photodiode array detection, Journal of Separation Science, 35 (2012) 2599-2607; E. Karageorgou, A. Myridakis, E. G. Stephanou, V. Samanidou, Multiresidue LC-MS/MS analysis of cephalosporins and quinolones in milk following ultrasound-assisted matrix solid-phase dispersive extraction combined with the quick, easy, cheap, effective, rugged, and safe methodology, Journal of Separation Science, 36 (2013) 2020-2027; E. Karageorgou, M. Armeni, I. Moschou, V. Samanidou, Ultrasound-assisted dispersive extraction for the high pressure liquid chromatographic determination of tetracyclines residues in milk with diode array detection, Food Chemistry, 150 (2014) 328-334).

All milk samples were initially tested as blanks to confirm that no CAP was present in the samples. Milk samples (containing 3.5% or 1.5% fat) were spiked with CAP, equilibrated at room temperature for 1 hour and then centrifuged at 1900 g for 15 min. The cream layer of the milk sample was carefully removed from the solution. The supernatant was collected for subsequent protein precipitation. For skim milk, no fat removal exercise was applied prior to protein precipitation.

A 5.0 g aliquot of skim milk and 8 mL of acetonitrile was placed in a 15 mL test tube to promote protein precipitation. The mixture was vortexed for 5 min and then allowed to stand for 10 min at room temperature. The contents were centrifuged at 1900 g for 15 min and the supernatant was collected and subsequently loaded on SPE cartridges comprising the sol-gel MIP or the sol-gel NIP as provided herein.

In order to adopt the most efficient protein precipitation strategy, different protein precipitation agents were evaluated including, for example, acetonitrile, formic acid (25%), and acetic acid (25%). Imprinting factors and extraction recovery values were checked comparatively. Acetonitrile was chosen for further experiments.

Calibration curves based on peak area versus concentration were constructed from five calibration levels. Samples were prepared by spiking blank milk sample matrix with CAP corresponding to concentrations of 50-5000 μg/kg. Lower concentrations (0.1-50 μg/kg) were analysed by LC-MS.

Repeatability, intermediate precision, and accuracy assays were performed at three concentration levels (100, 200 and 300 μg/kg). Blank milk samples were spiked with CAP and the recovery of CAP was calculated using the calibration curves. Five measurements were used for within-day repeatability assay. Intermediate reproducibility (between-day) was studied in a period of three days, by triplicate analysis. Recovery of CAP was calculated using the calibration curves.

Limits of detection and quantitation were based on the S/N ratio. The CCα and CCβ were calculated from ten blank milk samples quantified against the calibration curve from the linearity testing (T.E. Commission, Commission Decision (EU) 657/2002, L 221/8, of 12 Aug. 2002, implementing Council Directive 96/23/EC concerning the performance of analytical methods and the interpretation of results, (notified under document number C(2002) 3044), Official Journal of the European Communities, L 221 (2002) 8-36).

As for the applicability to real samples, five samples of three different types of milk samples, e.g., full-fat (3.5% fat) milk, semi-skim milk (1.5% fat), and skim (0% fat), were analysed using the MIPSPE method developed herein.

The analytical features of the synthesis methods provided herein such as linear range of the calibration curve, limit of detection (LOD), and precision were also examined. The calibration graph was linear in the range of 0.5-20 ng/mL of chloramphenicol. The equation for the calibration curve was: $y=0.0396x+0.0048$, $R^2=0.9981$ for standard solutions (x=ng/μL) and $y=9.8\times10.6x+0.00472$, $R^2=0.9926$ for milk (x=μg/kg).

The LOD was calculated based on 3 times the signal-to-noise (S/N) ratio and the limit of quantitation (LOQ) was calculated as 10 times the S/N ratio.

Figure 8A:
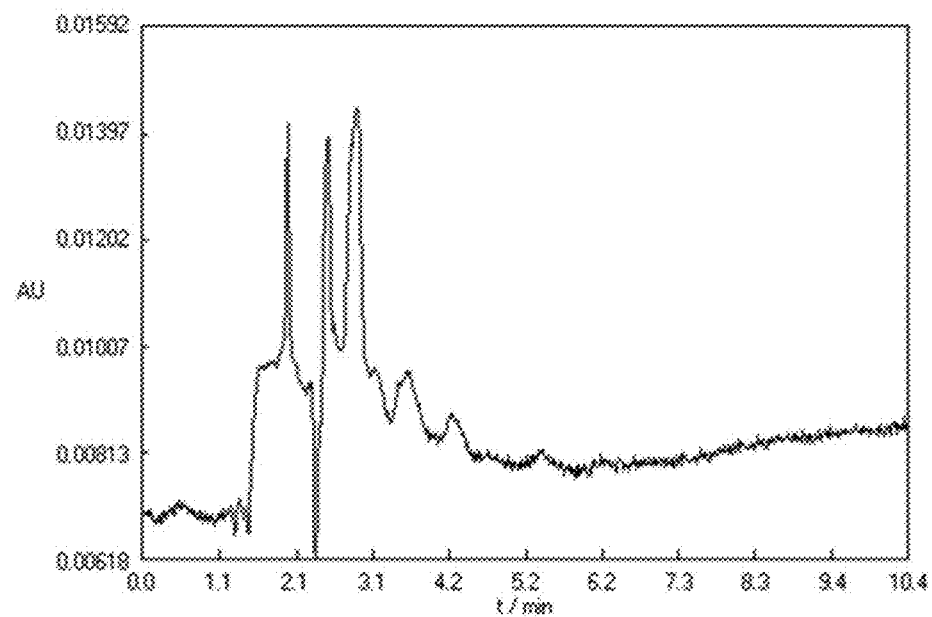
FIGS. 8A-8B illustrate chromatogram of (8A) a blank sample and (8B) a spiked milk sample obtained using the HPLC-UV method.
Figure 8B:
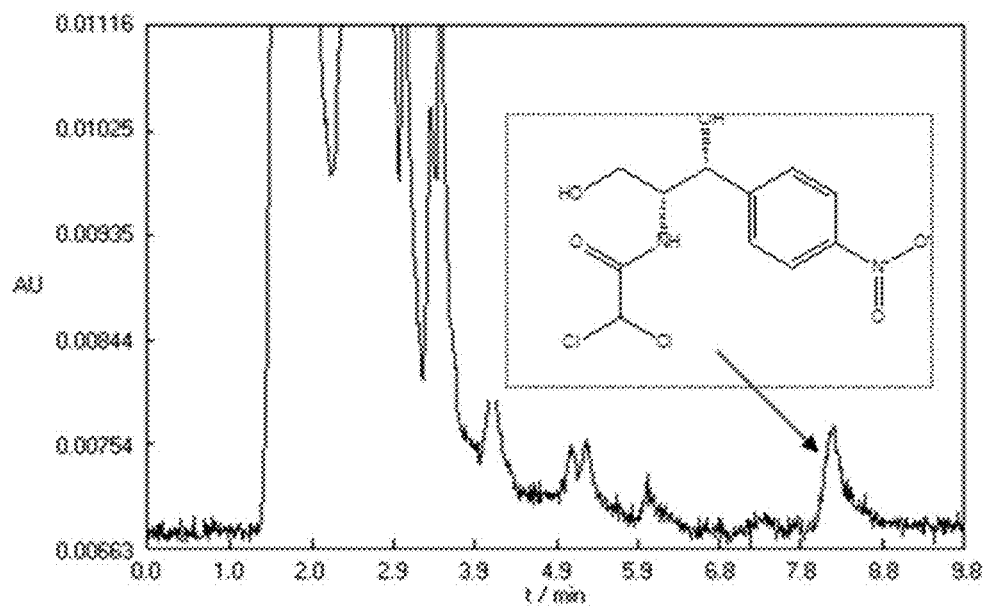
Figure 9A:
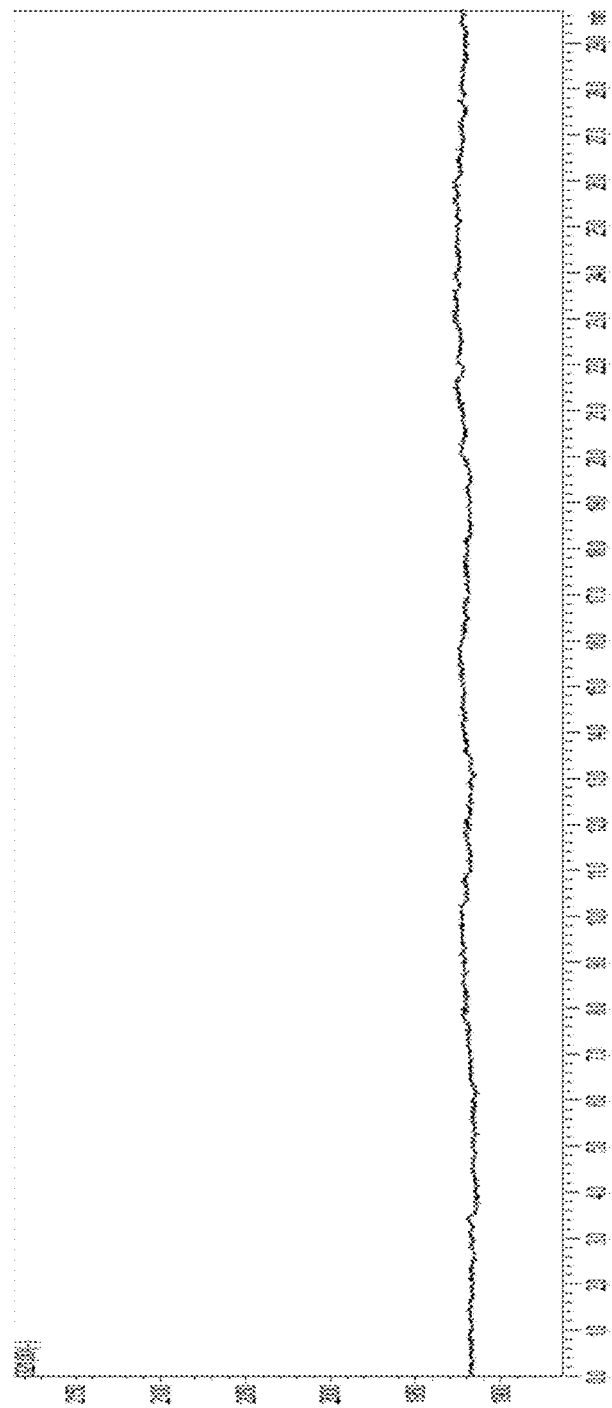
FIGS. 9A-9D illustrate LC-MS chromatogram of (9A) a blank sample, (9B) a spiked milk sample at 50 µg/kg (9C) an SIM spectrum, and (9D) a full-scan spectrum, respectively.
Figure 9B:
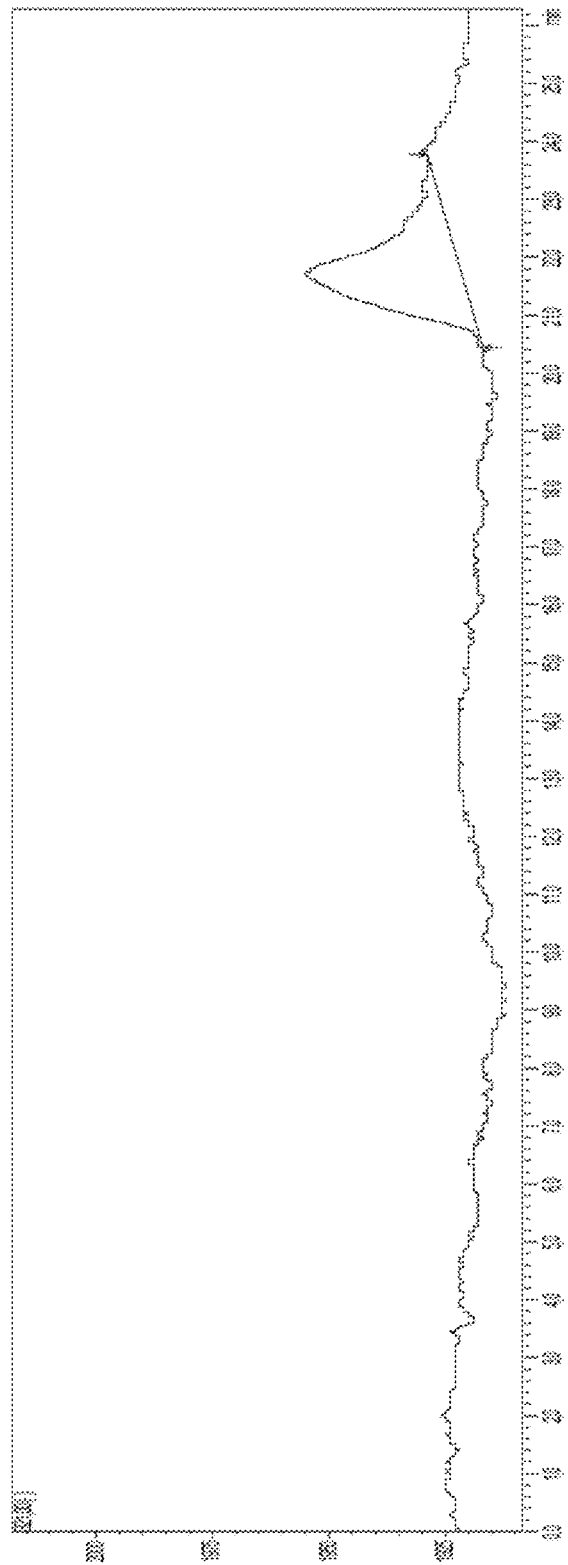
Figure 9C:
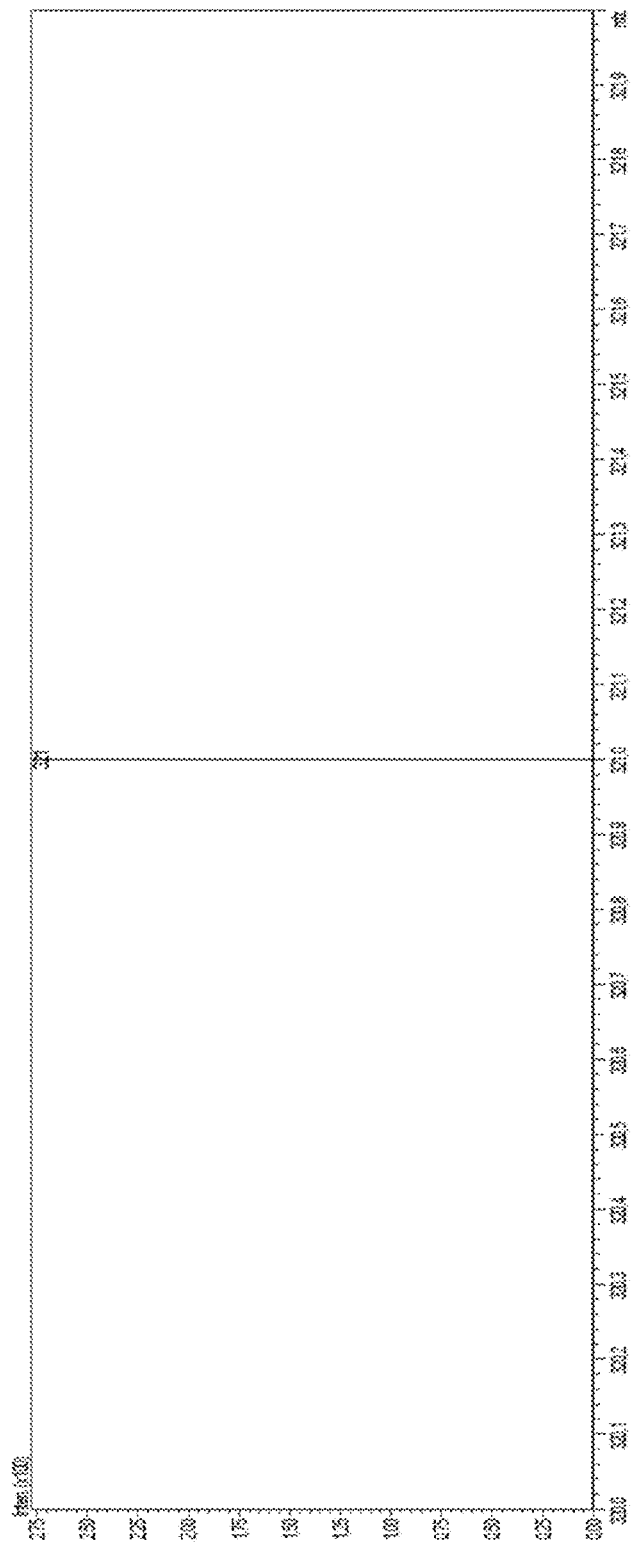
Figure 9D:
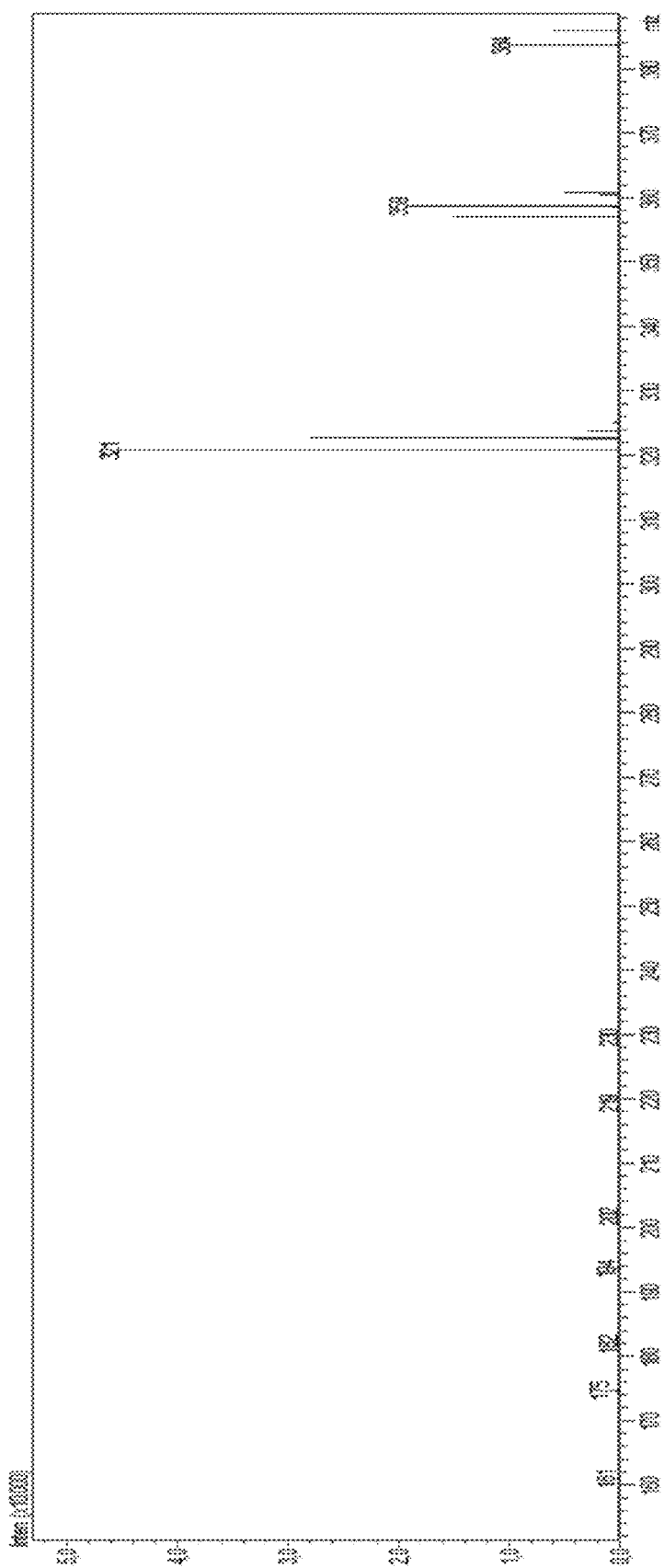

FIGS. 8A-8B illustrate a blank and a spiked milk chromatogram, respectively, obtained by the HPLC-UV method. Since CAP is an illicit substance, there is no maximum required level (MRL). The maximum required performance level (MRPL) of CAP, on the other hand, is 0.3 µg/kg, which can be reached only by using the LC-MS method (FIGS. 9A and 9B).

Decision Limit CCα and Detection Capacity CCβ Values were Determined

Repeatability, intermediate precision, and accuracy of the synthesis methods provided herein were examined at three levels, namely, at 100 µg/kg, 200 µg/kg, and 300 µg/kg. The relative standard deviation (RSD) of the within-day and between-day assays was lower than 11% and 13% respectively, showing good precision.

Accuracy was calculated by relative recovery and found to be in the range of 89-97% for within-day assay and 85-106% for between-day assay. Table 4 summarizes the analytical performance data.

TABLE 4

Validation parameters of the MISPE method for the determination of CAP in milk.

| Validation parameters | Value |
|---|---|
| Linear range µg/kg | 50-5000 |
| Linearity $R^2$ | 0.9926 |
| Slope | $9.78 \times 10^{-6}$ |
| Intercept | 0.0047 |
| LOD (LC-UV) S/N = 3.3 | 17 µg/kg |
| LOD (LC-MS) S/N = 3.3 | 0.1 µg/kg |
| LOQ (LC-UV) S/N = 10 | 50 µg/kg |
| LOQ (LC-MS) S/N = 10 | 0.3 µg/kg |
| Intra-assay precision n = 5 at 3 concentration levels | 89-97% |
| RSD % | <11% |
| Inter assay precision n = 3 × 3 at 3 concentration levels | 85-106% |
| RSD % | <13% |

Example 13—Performance Comparison with Other CAP-Imprinted Polymers

Considering the importance of monitoring the presence of CAP to ensure food safety, quality, and consumer protection, a large number of CAP-imprinted polymers have been developed over the last couple of years. However, all of these MIPs were prepared using organic synthesis approach and were used in different food and biological sample matrices. Table 5 reveals the important analytical figures of merits of selected MIPs used as extraction sorbent materials compared to the MIP sorbent obtained using the methods of the subject invention by sol-gel synthesis approach.

TABLE 5

Performance comparison of chloramphenicol imprinted molecularly imprinted polymers in different sample matrices.

| Sample Matrix | Analytical Instrument | Extraction Method | Imprinting Factor | Adsorption Capacity (mg/g) | Limit of Detection (ng/g) |
|---|---|---|---|---|---|
| Honey[a] | LC-MS/MS | Magnetic SPE | 1.375 | 5.53 | 0.047 |
| Urine[b] | GC-MS | MISPE | N/A | N/A | 0.06 |
| Honey | | | | | 0.06 |

TABLE 5-continued

Performance comparison of chloramphenicol imprinted molecularly imprinted polymers in different sample matrices.

| Sample Matrix | Analytical Instrument | Extraction Method | Imprinting Factor | Adsorption Capacity (mg/g) | Limit of Detection (ng/g) |
|---|---|---|---|---|---|
| Water | | | | | 0.005 |
| Milk | | | | | 0.03 |
| Milk[c] | LC-ESI-MS/MS | MISPE | N/A | N/A | 0.06 |
| Honey[d] | LC-MS/MS | MISPE | 2.43 | N/A | 0.03 |
| Urine | | | | | 0.03 |
| Milk[e] | HPLC-UV | MISPE | 1.38 | 2.22 | |
| Honey[f] | HPLC-UV | MISPE | 2.2 | N/A | 100* |
| Milk[g] | HPLC-UV LC-MS | MISPE | 9.7 | 23.0 | 7* 1 |

References in Table 5:
[a] L. G. Chen, B. Li, Magnetic molecularly imprinted polymer extraction of chloramphenicol from honey, Food Chemistry, 141 (2013) 23-28.
[b] M. Rejtharova, L. Rejthar, Determination of chloramphenicol in urine, feed water, milk and honey samples using molecular imprinted polymer clean-up, Journal of Chromatography A, 1216 (2009) 8246-8253.
[c] R. Mohamed, J. Richoz-Payot, E. Gremaud, P. Mottier, E. Yilmaz, J. C. Tabet, P. A. Guy, Advantages of molecularly imprinted polymers LC-ESI-MS/MS for the selective extraction and quantification of chloramphenicol in milk-based matrixes. Comparison with a classical sample preparation, Analytical Chemistry, 79 (2007) 9557-9565.
[d] B. Boyd, H. Bjork, J. Billing, O. Shimelis, S. Axelsson, M. Leonora, E. Yilmaz, Development of an improved method for trace analysis of chloramphenicol using molecularly imprinted polymers, Journal of Chromatography A, 1174 (2007) 63-71.
[e] X. Z. Shi, A. B. Wu, S. L. Zheng, R. X. Li, D. B. Zhang, Molecularly imprinted polymer microspheres for solid-phase extraction of chloramphenicol residues in foods, Journal of Chromatography B-Analytical Technologies in the Biomedical and Life Sciences, 850 (2007) 24-30.
[f] C. Schirmer, H. Meisel, Synthesis of a molecularly imprinted polymer for the selective solid-phase extraction of chloramphenicol from honey, Journal of Chromatography A, 1132 (2006) 325-328.
[g] the subject invention.

*LOD did not meet MRPL of 0.3 ng/g set forth by European Commission Decision 2003 (E. Commission, Commission Decision (EU) 181/2003, L 71/17 of 13 Mar. 2003, Amending Decision 2002/657/EC as regards the setting of minimum required performance limits (MRPLs) for certain residues in food animal origin (notified under document number C(2003) 764, Official Journal European Union, 2003, pp. 17-18).

The comparison data demonstrates the superior performance of CAP imprinted sol-gel MIP sorbent over other reported MIPs and justifies its application in food safety and quality monitoring regimes.

All patents, patent applications, provisional applications, and publications referred to or cited herein are incorporated by reference in their entirety, including all figures and tables, to the extent they are not inconsistent with the explicit teachings of this specification.

The description herein of any aspect or embodiment of the invention using terms such as "comprising," "having," "including" or "containing" with reference to an element or elements is intended to provide support for a similar aspect or embodiment of the invention that "consists of," "consists essentially of," or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The term "consisting essentially of," as used herein, limits the scope of the ingredients and steps to the specified materials or steps and those that do not materially affect the basic and novel characteristic(s) of the present invention.

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A method of synthesizing a molecularly imprinted polymer (MIP) matrix, comprising:
mixing chloramphenicol (CAP) with more than one sol-gel precursor to form a polymer complex, wherein the sol-gel precursors comprise saline groups;
hydrolyzing the sol-gel precursors and a cross-linking agent with a hydrolytic agent in the presence of a reaction catalyst;
combining the hydrolyzed sol-gel precursors with the polymer complex;
allowing the sol-gel polymer complex to form surrounding the target analyte; and
extracting the target analyte using a solvent, leaving behind molecular cavities in the polymer network that are complementary in size, shape, and functionality to the target analyte.

2. The method according to claim 1, the sol-gel precursors being 3-aminopropyltriethoxysilane and triethoxyphenylsilane.

3. The method according to claim 1, the cross-linking agent being tetramethyl orthosilicate.

4. The method according to claim 1, the reaction catalyst being an acid.

5. The method according to claim 4, the catalyst being hydrochloric acid.

6. The method according to claim 1, the hydrolytic agent being water.

7. The method according to claim 1, the solvent being selected from methanol, ethanol, isopropanol, formic acid, acetonitrile, acetone, and mixtures thereof.

8. A sol-gel MIP sorbent material prepared using the method according to claim 1.

9. The material according to claim 8, said material being capable of detecting the target analyte in a sample but being indifferent to other species present in the same sample.

10. A method of detecting CAP in a fluid sample, comprising:
providing a sol-gel polymer sorbent material imprinted molecularly with CAP, the sorbent material being prepared according to claim 1 passing the fluid sample through the sorbent material; and
detecting CAP in the eluent of the sorbent material.

11. The method according to claim 10, performed in an apparatus selected from a syringe and a solid-phase extraction cartridge.

12. The method according to claim 10, the sample being selected from physiological fluids, forensic specimens, environmental pollutants, food samples, beverage samples, pharmaceutical samples, chemical samples, drug residues and metabolites thereof, and poison residues and metabolites thereof.

13. The method according to claim 10, further comprising quantification of the concentration of the CAP in the sample.

14. A method of detecting chloramphenicol (CAP) in a sample, comprising:
providing a molecularly imprinted polymer (MIP) sorbent material, the sorbent material being prepared via a sol-gel process employing CAP as the target analyte, 3-aminopropyltriethoxysilane and triethoxyphenylsilane as sol-gel precursors, tetramethyl orthosilicate as a cross-linking agent, hydrochloric acid as a reaction catalyst, water as a hydrolytic agent, and isopropanol and methanol as solvents;
packaging dried MIP sorbent material in an extraction apparatus selected from a syringe and a solid-phase extraction cartridge;
providing a fluid sample;
passing the fluid sample through the extraction apparatus; and
quantifying the concentration of CAP in the eluent of the MIP sorbent material.

15. The method according to claim 14, the eluent of the sorbent material being obtained using a solvent selected from methanol, ethanol, isopropanol, formic acid, acetonitrile, acetone, and a mixture thereof.

16. The method according to claim 14, the sample being selected from physiological fluids, forensic specimens, environmental pollutants, food samples, beverage samples, pharmaceutical samples, chemical samples, drug residues and metabolites thereof, and poison residues and metabolites thereof.

* * * * *